United States Patent [19]

Knjaschewitsch et al.

[11] Patent Number: 5,378,896

[45] Date of Patent: Jan. 3, 1995

[54] HARMFUL SOLAR RADIATION DETECTION DEVICE

[76] Inventors: Sascha R. Knjaschewitsch, PO Box 863, Bernon, British Columbia V1T 6M8; David A. Petch, PO Box 193, 41 Riverview Place, Lasalle, Manitoba, R0G 1B0, both of Canada

[21] Appl. No.: 177,561

[22] Filed: Jan. 5, 1994

Related U.S. Application Data

[63] Continuation-in-part of Ser. No. 85,256, Jul. 1, 1993, abandoned, which is a continuation of Ser. No. 845,703, Mar. 4, 1992, abandoned.

[51] Int. Cl.⁶ .................................................. G01J 1/50
[52] U.S. Cl. ................................. 250/474.1; 250/372
[58] Field of Search ............................ 250/474.1, 372

[56] References Cited

U.S. PATENT DOCUMENTS

| | | | |
|---|---|---|---|
| 3,590,772 | 7/1971 | Boone | 250/372 |
| 3,787,687 | 1/1974 | Trumble | 250/474.1 |
| 3,903,423 | 9/1975 | Zweig | 250/474.1 |
| 4,788,433 | 11/1988 | Wright | 250/474.1 |
| 4,818,491 | 4/1989 | Fariss | 250/372 |
| 4,863,282 | 9/1989 | Rickerson | 250/372 |
| 4,985,632 | 1/1991 | Bianco et al. | 250/372 |
| 5,028,792 | 7/1991 | Mullis | 250/474.1 |
| 5,084,623 | 1/1992 | Lewis et al. | 250/474.1 |
| 5,117,116 | 5/1992 | Bannard et al. | 250/474.1 |

OTHER PUBLICATIONS

Delpalma, Mark S. "Multi-Color Ultraviolet Radiation Measurement Device", WO 89/06347, 13 Jul. 1994.

*Primary Examiner*—Dzierzynski Paul M.
*Assistant Examiner*—Drew A. Dunn

[57] ABSTRACT

A harmful solar radiation detection apparatus includes a first fluorescent composition comprised of a blend of a first fluorescent material and a second fluorescent material contained in a first retainer. The first fluorescent material is capable of absorbing radiation having a wavelength less than 300 nm and is capable of fluorescing at a first fluorescent wavelength above 300 nm upon absorption of the radiation less than 300 nm. The second fluorescent material is capable of absorbing radiation at the first fluorescent wavelength and is capable of fluorescing at a second fluorescent wavelength which is a visible wavelength. A second fluorescent composition is comprised of the second fluorescent material and is contained in a second retainer. A housing assembly supports and houses the first retainer and the second retainer such that the first fluorescent composition and the second fluorescent composition are capable of being exposed to sunlight. A first filter may be placed between sunlight and the first fluorescent composition, and a second filter may be placed between sunlight and the second fluorescent composition. The first and second filters filter out wavelengths above 300 nm. A viewing window is defined by the housing assembly and permits a viewer to view and compare colors of the first fluorescent composition and the second fluorescent composition upon exposure to sunlight. The sunlight-exposed first fluorescent composition serves as an indicator of exposure to harmful solar radiation; and the sunlight-exposed second fluorescent composition serves as a control.

10 Claims, 4 Drawing Sheets

HARMFUL SOLAR RADIATION DETECTION DEVICE

RELATED APPLICATION

This application is a continuation-in-part of copending application, Ser. No. 08/085,256, filed Jul. 1, 1993, which, in turn, is a continuation of prior application Ser. No. 07/845,703, filed Mar. 4, 1992, now both abandoned.

BACKGROUND OF THE INVENTION

1. Field of the Invention

The present invention relates generally to solar radiation detection devices, and more particularly, to a harmful radiation detector construction which indicates to a user when it is safe to expose his skin to solar radiation.

2. Description of the Prior Art

It has been clinically proven that exposure of the human body to solar radiation substantially increases the risk of developing skin cancer. The prevention of skin cancer up to the present has been accomplished mainly through the use of sunscreen applicators which allow longer exposure of the human skin to the sun's radiation. However, on those days when there is unscreened harmful radiation (caused by depletion of ozone in the atmosphere), it is not possible to detect these harmful rays and the consumer, using his or her own discretion must make a decision as to how long to remain exposed to the sun's rays. This is particularly important in areas of North America and Australia where it has been scientifically documented that there are "wandering holes" in the ozone layer. As a direct result of these holes, there is an increased rate of skin cancer and accordingly, there exists a continuing need for feasible devices which would permit a consumer to determine when substantially harmful solar radiation is present. In this respect, the present invention substantially fulfills this need.

SUMMARY OF THE INVENTION

In view of the foregoing disadvantages inherent in the known types of solar radiation detecting devices now present in the prior art, the present invention provides an improved solar radiation protecting device wherein the same can be utilized by a consumer to determine when substantially harmful solar radiation is present. As such, the general purpose of the present invention, which will be described subsequently in greater detail, is to provide a new and improved solar radiation detection device which has all of the advantage of the prior art solar radiation detection devices and none of the disadvantages.

To attain this, the present invention essentially comprises a detector which is designed to sense the presence of harmful radiation which has been clinically proven to increase the risk of developing skin cancer. The increase of harmful solar radiation, which is cause by ozone depletion in the atmosphere, causes chemicals to change color. Certain colors can indicate a safe suntanning environment while other colors represent a drastic increase in risk for skin cancer.

In accordance with one aspect of the invention, a harmful solar radiation detection apparatus includes a first fluorescent composition comprised of a blend of a first fluorescent material and a second fluorescent material. The first fluorescent material is capable of absorbing radiation having a wavelength less than 300 nm and is capable of fluorescing at a first fluorescent wavelength above 300 nm upon absorption of the radiation less than 300 nm. The second fluorescent material is capable of absorbing radiation at the first fluorescent wavelength and is capable of fluorescing at a second fluorescent wavelength which is a visible wavelength. A second fluorescent composition is comprised of the second fluorescent material. A first retainer retains the first fluorescent composition. A second retainer retains the second fluorescent composition. A housing assembly for supports and houses the first retainer and the second retainer such that the first fluorescent composition and the second fluorescent composition are capable of being exposed to sunlight.

A first filter is placed between sunlight and the first fluorescent composition. The first filter filters out wavelengths above 300 nm. A second filter is placed between sunlight and the second fluorescent composition. The second filter filters out wavelengths above 300 nm. A viewing window is defined by the housing assembly and permits a viewer to view the first fluorescent composition and the second fluorescent composition upon exposure to sunlight. The viewing window includes a magnifying member.

The first fluorescent material is composed of triphenylene which absorbs radiation below 300 nm and which fluoresces at a first fluorescent wavelength at 365 nm. The second fluorescent material is composed of 3-amino-fluoranthene which absorbs radiation at the first fluorescent wavelength. The second fluorescent material also fluoresces at a second fluorescent wavelength at 515 nm, which is a visible yellow in color.

In accordance with another aspect of the present invention, a method of detecting harmful solar radiation is provided which includes the steps of:

(1) obtaining a quantity of a first fluorescent composition comprised of a blend of a first fluorescent material and a second fluorescent material, wherein the first fluorescent material is capable of absorbing radiation having a wavelength less than 300 nm and is capable of fluorescing at a first fluorescent wavelength above 300 nm upon absorbing the radiation less than 300 nm, and wherein the second fluorescent material is capable of absorbing radiation at the first fluorescent wavelength and is capable of fluorescing at a second fluorescent wavelength which is a visible wavelength;

(2) obtaining a quantity of a second fluorescent composition comprised of the second fluorescent material;

(3) exposing both the first fluorescent composition and the second fluorescent composition to sunlight; and (4) comparing respective colors of the sunlight-exposed first fluorescent composition and the sunlight-exposed second fluorescent composition, such that the sunlight-exposed second fluorescent composition serves as a control, and the sunlight-exposed first fluorescent composition serves as an indicator of exposure to harmful solar radiation.

In accordance with another aspect of the method of the invention, an additional step provides for filtering sunlight through a first filter for providing the first fluorescent composition with filtered sunlight. The first filter filters out wavelengths above 300 nm. In addition, filtering sunlight through a second filter provides the second fluorescent composition with filtered sunlight. The second filter filters out wavelengths above 300 nm.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

Further, the purpose of the foregoing Abstract is to enable the U.S. Patent and Trademark Office and the public generally, and especially the scientists, engineers and practitioners in the art who are not familiar with patent or legal terms of phraseology, to determine quickly from a cursory inspection the nature and essence of the technical disclosure of the application. Accordingly, the Abstract is neither intended to define the invention or the application, which only is measured by the claims, nor is it intended to be limiting as to the scope of the invention in any way.

It is therefore an object of the present invention to provide a new and improved harmful solar radiation detection device which has all of the advantages of the prior art and none of the disadvantages.

It is another object of the present invention to provide a new an improved harmful solar radiation detection device which may be easily and efficiently manufactured and marketed.

It is a further objective of the present invention to provide a new and improved harmful solar radiation detection device which is of durable and reliable construction.

An even further object of the present invention is to provide a new and improved harmful solar radiation detection device which is susceptible of a low cost of manufacture with regard to both materials and labor, and which accordingly is then susceptible of low prices of sale to the consuming public, thereby making such harmful solar radiation detection device available to the buying public.

Still yet a further object of the present invention is to provide a new and improved solar radiation detection device which provides in the apparatuses and methods of the prior art some of the advantages thereof, while simultaneously overcoming some of the disadvantages normally associated therewith.

It is still a further object of the present invention is to provide a new and improved solar radiation detection device which utilizes a change in visible color to indicate when harmful solar radiation is present.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF THE DRAWINGS

The invention will be better understood and the above objects as well as objects other than those set forth above will become more apparent after a study of the following detailed description thereof. Such description makes reference to the annexed drawings wherein.

DESCRIPTION OF THE PREFERRED EMBODIMENT

Figure 1:
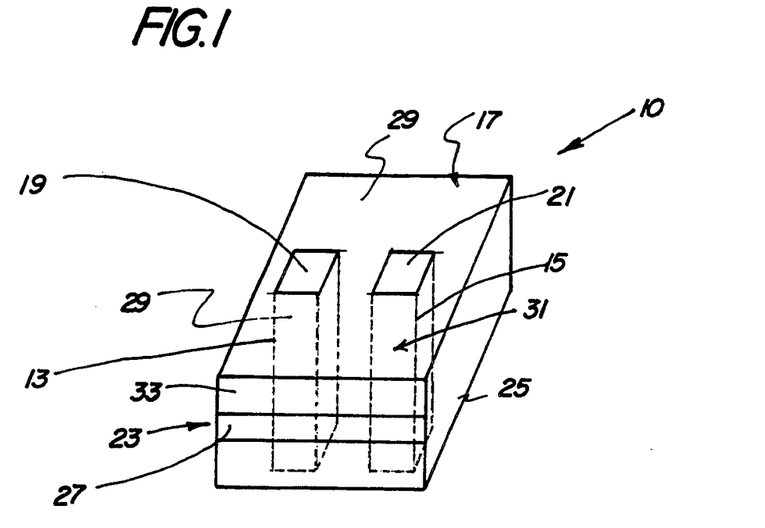
FIG. 1 is a perspective view of a first preferred embodiment of the harmful solar radiation detection device of the invention.
Figure 2:
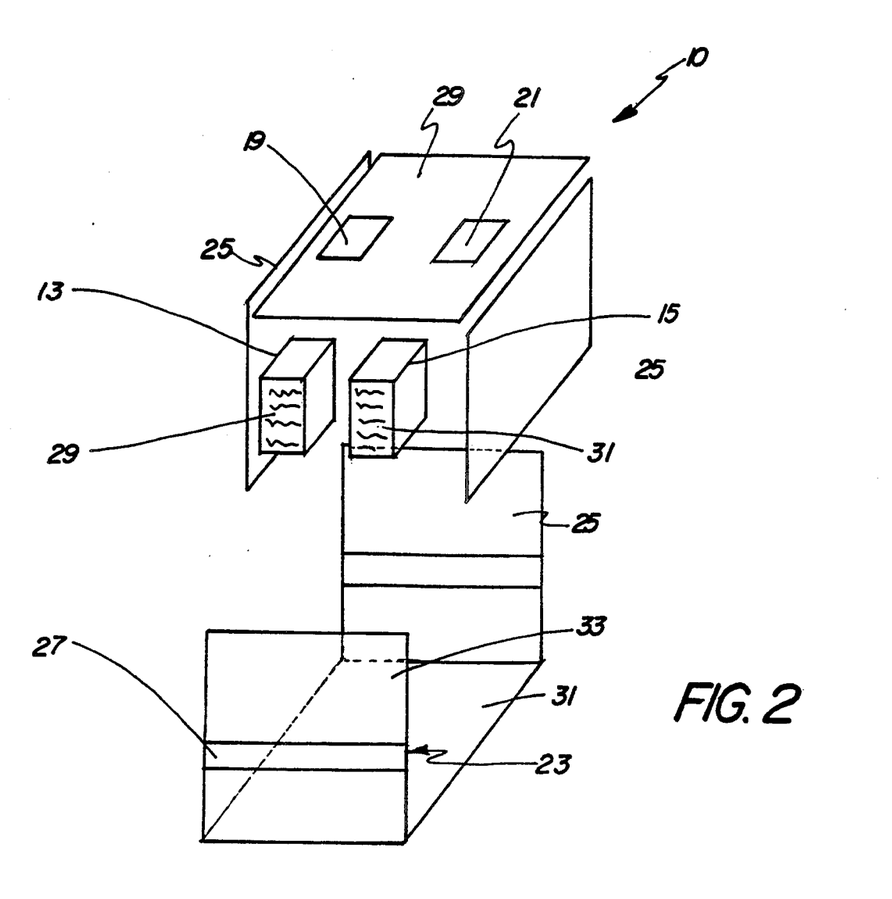
FIG. 2 is an exploded view of the embodiment shown in FIG. 1

With reference now to the drawings, and in particular to FIGS. 1 and 2 thereof, a first embodiment of a new and improved harmful solar radiation detection device embodying the principles and concepts of the present invention and generally designated by the reference numeral 10 will be described.

In this regard, all of the embodiments of the present invention facilitate the detection of harmful wavelengths of sunlight which increase the promotion of skin cancer. The theory behind the present invention is based upon the detection of wavelengths which would normally be filtered out by an intact ozone layer. Due to ozone destruction by chloro-fluorocarbons (CFC's), these harmful rays greatly increase the risk of getting skin cancer by individuals exposed thereto. This of course, does not mean that prolonged exposure to "normal" sunlight will not cause skin cancer, but rather that the potential for skin cancer greatly increases in direct response to ozone destruction.

In the first embodiment of the invention, two chemicals are used in combination to provide a chemical composition that provides a color change due to the detection of light having a wavelength less than 290 nm. The two chemicals produce a color change due to their fluorescent properties.

Fluorescence radiation from organic compounds has wavelengths found in the region from 300 nanometers (nm) to 650 nm. A solution which emits fluorescence radiation when excited is termed a scintillation fluid. With the invention, a chemical composition is provided which is a ternary system composed of a solvent (donor) and two solutes (acceptors M and N). More specifically, triphenylene absorbs light at 265 nm and fluoresces at 368 nm. In addition, 3-amino-fluoranthene absorbs light at 365 nm and fluoresces at 515 nm which is a yellow color. In operation, with the triphenylene and the 3-amino-fluoranthene blended in a solvent, e.g. light having a wavelength below 300 nm is absorbed by the triphenylene and causes fluorescence at 365 nm. The wavelength of 365 nm is absorbed by the 3-amino-fluoranthene which fluoresces at 515 nm which is yellow in color.

FIGS. 1 and 2 illustrate a first embodiment of the invention of the harmful solar radiation detection apparatus which includes a first fluorescent composition 29 comprised of a blend of a first fluorescent material and a second fluorescent material. The first fluorescent material is capable of absorbing radiation having a wavelength less than 300 nm and is capable of fluorescing at a first fluorescent wavelength above 300 nm upon absorption of the radiation less than 300 nm. The second fluorescent material is capable of absorbing radiation at the first fluorescent wavelength and is capable of fluorescing at a second fluorescent wavelength which is a visible wavelength. A second fluorescent composition 31 is comprised of the second fluorescent material. A first retainer 13 retains the first fluorescent composition 29. A second retainer 15 retains the second fluorescent composition 31. The first retainer 13 and the second retainer 15 are sealed transparent cells made from quartz. housing assembly 17 for supports and houses the first retainer 13 and the second retainer 15 such that the first fluorescent composition 29 and the second fluorescent composition 31 are capable of being exposed to sunlight.

A first filter 19 is placed between sunlight and the first fluorescent composition 29. The first filter 19 filters out wavelengths above 300 nm. A second filter 21 is placed between sunlight and the second fluorescent composition 31. The second filter 21 filters out wavelengths above 300 nm. A viewing window 23 is defined by the housing assembly 17 and permits a viewer to view the first fluorescent composition 29 and the second fluorescent composition 31 upon exposure to sunlight.

More specifically, the housing assembly 17 includes opaque wall panels 25, a top panel 29, a front panel 33, and a floor panel 31 for shielding the first retainer 13 and the second retainer 15 therein. The top panel 29 has cut out portions for the first filter 19 and the second filter 21. The front panel 33 has a cut out portion for the viewing window 23 for viewing the colors of the first fluorescent composition 29 and the second fluorescent composition 31. The viewing window 23 includes a magnifying member 27.

The first fluorescent material is composed of triphenylene which absorbs radiation below 300 nm, e.g. at 265 nm, and which fluoresces at a first fluorescent wavelength at 365 nm which is included in an absorption range which includes an absorption peak at 368 nm.

The second fluorescent material is composed of 3-amino-fluoranthene which absorbs radiation at the first fluorescent wavelength which is in the range that has an absorption peak at 365 nm. The second fluorescent material also fluoresces at a second fluorescent wavelength at 515 nm, which is a visible yellow in color.

The triphenylene and the 3-amino-fluoranthene are dispersed in cyclohexane which is inert and transparent to ultraviolet radiation which is above the wavelength of 240 nm. The concentration of the triphenylene is 0.1 grams/liter. The concentration of the 3-amino-fluoranthene is 0.25 grams/liter.

Absorbance data for the triphenylene and the 3-amino-fluoranthene is found in standard literature including *Handbook of fluorescence spectra of aromatic molecules,* 2nd edition, by Isadore Berlman, (1971), Academic Press, Inc., New York and London. Other suitable fluorescent materials are found in this publication.

In accordance with another aspect of the present invention, a method of detecting harmful solar radiation is provided which includes the steps of:

(1) obtaining a quantity of a first fluorescent composition 29 comprised of a blend of a first fluorescent material and a second fluorescent material, wherein the first fluorescent material is capable of absorbing radiation having a wavelength less than 300 nm and is capable of fluorescing at a first fluorescent wavelength above 300 nm upon absorbing the radiation less than 300 nm, and wherein the second fluorescent material is capable of absorbing radiation at the first fluorescent wavelength and is capable of fluorescing at a second fluorescent wavelength which is a visible wavelength;

(2) obtaining a quantity of a second fluorescent composition 31 comprised of the second fluorescent material;

(3) exposing both the first fluorescent composition 29 and the second fluorescent composition 31 to sunlight; and (4) comparing respective colors of the sunlight-exposed first fluorescent composition 29 and the sunlight-exposed second fluorescent composition 31, such that the sunlight-exposed second fluorescent composition 31 serves as a control, and the sunlight-exposed first fluorescent composition 29 serves as an indicator of exposure to harmful solar radiation.

More specifically, in operation, when the sunlight-exposed first fluorescent composition 29 and the sunlight-exposed second fluorescent composition 31 show substantially the same color, then the fluorescent materials were not substantially exposed to harmful solar radiation. However, when the sunlight-exposed first fluorescent composition 29 shows perceptibly more color than the sunlight-exposed second fluorescent composition 31, then the fluorescent materials were exposed to harmful solar radiation.

In accordance with another aspect of the method of the invention, the step of filtering sunlight through a first filter 19 for provides the first fluorescent composition 29 with filtered sunlight. The first filter 19 filters out wavelengths above 300 nm. In addition, filtering sunlight through a second filter 21 for provides the second fluorescent composition 31 with filtered sunlight. The second filter 21 filters out wavelengths above 300 nm. Since the second filter 21 filters out all light above 300 nm, any light of lower wavelength will pass through the filter. With the first fluorescent composition 29, visible detection of wavelengths below 300 nm will occur because the fluorescence of the filtered-sunlight-exposed first fluorescent material will cause fluorescence of the filtered-sunlight-exposed second fluorescent material providing a visible light.

On the other hand, with the second fluorescent composition 31, there will be no visible detection of wavelengths below 300 nm since the second fluorescent material is the only light-emitting material present and requires absorption of light of 365 nm to produce a fluorescent emission. Exposure of both the first fluorescent composition 29 and the second fluorescent composition 31 to the filtered sunlight causes a detectable color difference between the first fluorescent composition 29 and the second fluorescent composition 31.

In contrast, when the sunlight does not contain radiation below a wavelength of 300 nm (because the ozone layer is intact), the filtered-sunlight-exposed first fluorescent composition 29 and the filtered-sunlight-exposed second fluorescent composition 31 show essentially the same color.

Still additional embodiments of the invention are shown in FIGS. 3-7. In this respect, where several shapes of the present invention are shown in the present application, it is to be understood that additional embodiments of the invention can take on any conceivable shape or form inasmuch as it basically involves two different know chemicals suspended in a crystal lattice structure, such as glass or a highly stress resistent plastic. This crystal lattice structure must be transparent, and the shapes may include that of a credit card, a charm bracelet, a circular disk on a suntan lotion bottle, or even a little strip on a wrist watch, to name just a few ideas.

Continuing with the theory involved with the present invention, it can be appreciated that ozone filter wavelengths of sun radiation which lie below 290 nm from the light spectrum, which allowing passage of longer wavelengths. Suntanning is usually carried out by individuals at wavelengths between 300 nm and 380 nm. These wavelengths are believed to be responsible for promoting skin cancer if exposed for prolonged periods of time. Any exposure to wavelength below 290 nm drastically increases the rate of skin cancer. A one percent decease in the ozone layer corresponds to an increase of two percent in harmful radiation, and this causes an increase in the development of skin cancer by five percent.

There are numerous well known chemicals which respond to changes in light wavelength by changing color or by reacting to a specific wavelength by changing to a specific color. Rather than sort through this plurality of light responsive, changeable color chemicals, the present invention will rely upon any two of these chemicals which will hereinafter be referred to respectively as chemicals X and Y. The two chemicals named X and Y are suspended in the aforementioned crystal lattice with the assumption that chemical X will produce, for example, a specific color when exposed to 280 nm. This specific color would preferably by a primary color, i.e., blue for example. Chemical Y will produce, for example, a specific color when exposed to 330 nm representing a "safe" radiation exposure range—provided that the exposure is for a reasonable period of time. Chemical Y could by way of example by yellow. Since chemical X requires a minimum energy of excitement of 280 nm to cause chemical change, its color will be blended in with the color of chemical Y to give a different color, i.e., green for example. More specifically, blue and yellow combined to give a green color.

Figure 3:
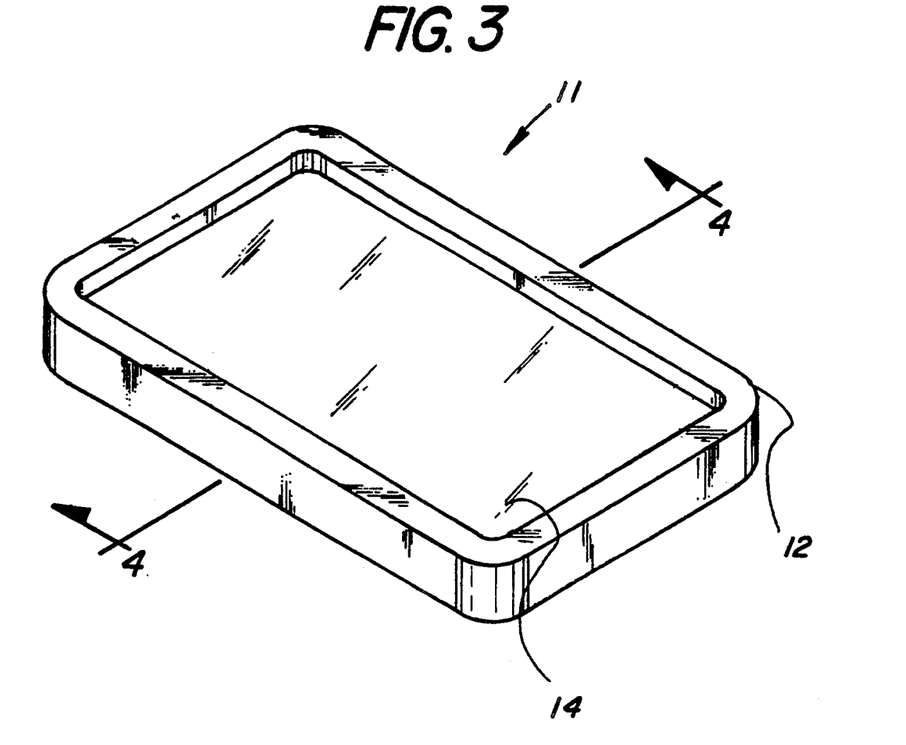
FIG. 3 is a perspective view showing the second preferred embodiment of the harmful solar radiation detection device of the invention.
Figure 4:
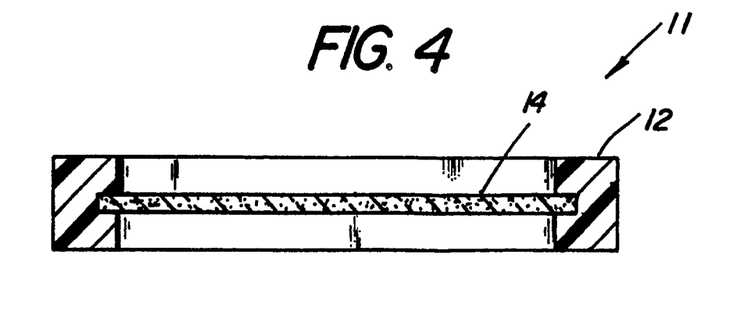
FIG. 4 is a cross-sectional elevational view of the harmful solar radiation detection device as viewed along line 4—4 of FIG. 3.

As shown in FIGS. 3 and 4, the second embodiment 11 of the invention is of a credit card shape and includes a peripheral support structure 12 into which is mounted a planar shaped crystal lattice structure 14 which is transparent to the sun's rays. As above mentioned, the crystal lattice structure 14 could be formed of glass or some other highly stress resistant plastic material as long as such material is crystal clear. The above described chemicals X and Y are interspersed within the crystal lattice structure 14 and, as long as safe solar radiation is being detected (300 nm to 380 nm) the chemical Y will change from clear to yellow due to the presence of light wavelengths in the 330 nm range. At the same time, the chemical X will still remain clear (uncolored) due to the failure to detect any light wavelengths in the 280 nm range. In the event that ozone depletion allows harmful radiation to penetrate the earth's atmosphere, the 280 nm range wavelengths will strike the crystal lattice structure 14 whereby the chemical X will change from a clear color to blue. Since the blue and yellow are intermixed or at least overlying one another, a green color will be produced which advises the user to get out of the sun.

Figure 5:
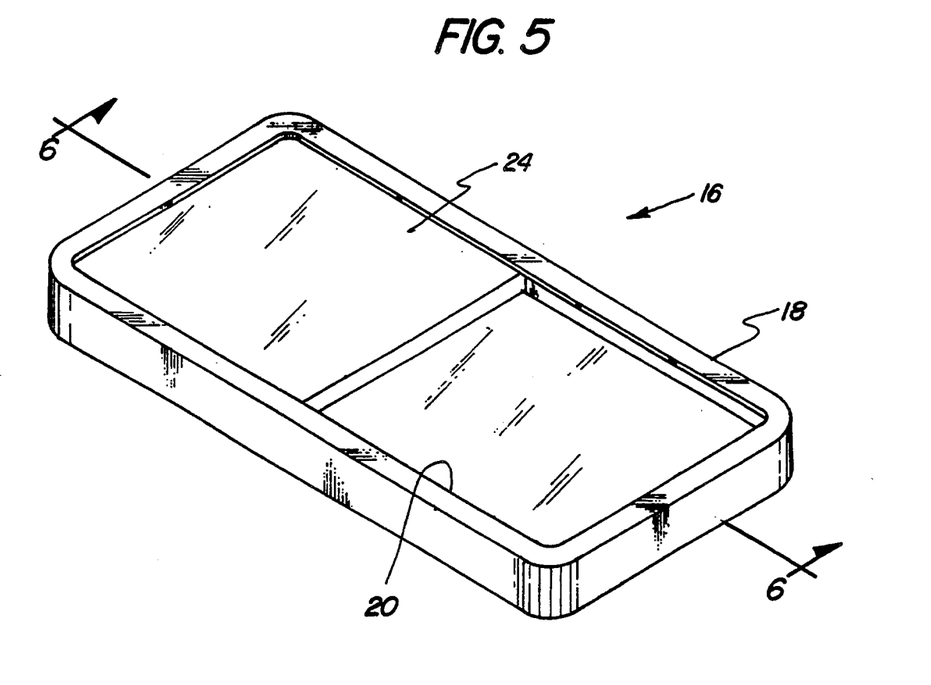
FIG. 5 is a perspective view of a third embodiment of the harmful solar radiation detection device.
Figure 6:
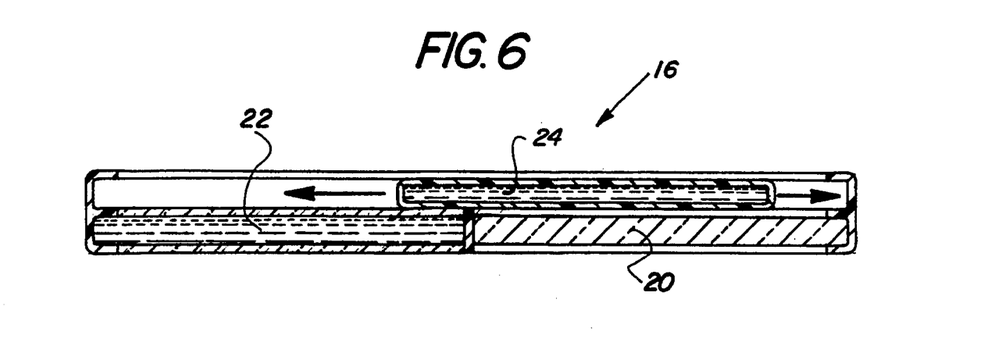
FIG. 6 is a cross-sectional elevational view of the harmful solar radiation detection device as viewed along line 6—6 of FIG. 5.

FIGS. 5 and 6 of the drawings illustrate a third embodiment of the present invention which is generally designated by the reference numeral 16. This embodiment also includes a peripheral support structure 18 which, as best shown in FIG. 4, includes a fixedly positioned clear plastic window 20, a crystal lattice structure 22 having in the chemical X impregnated therein and fixedly secured proximate thereto, and a slidable crystal lattice structure having the chemical Y impregnated therein. The slidable crystal lattice structure 24 is selectively positionable in front of the clear plastic window 20 or the crystal lattice structure 22. This embodiment 16 of the invention facilitates the detection of small amounts of harmful radiation which might occur due to the difficulty in detecting minor color changes. More specifically, presumably the lattice structure 24 would remain yellow in response to the presence of safe solar radiation having a wavelength of around 330 nm. In the event that some solar radiation in the 280 nm wavelength range is passing through the ozone layer, a slight color change may be present in the lattice structure 22 which would normally be hard to detect. By sliding the structure 24 backwards and forwards between the windows 20, 22, a user would more readily be able to detect a slight change from yellow to perhaps light green, thereby being provided with an indication of the presence of at least some harmful solar radiation.

Figure 7:
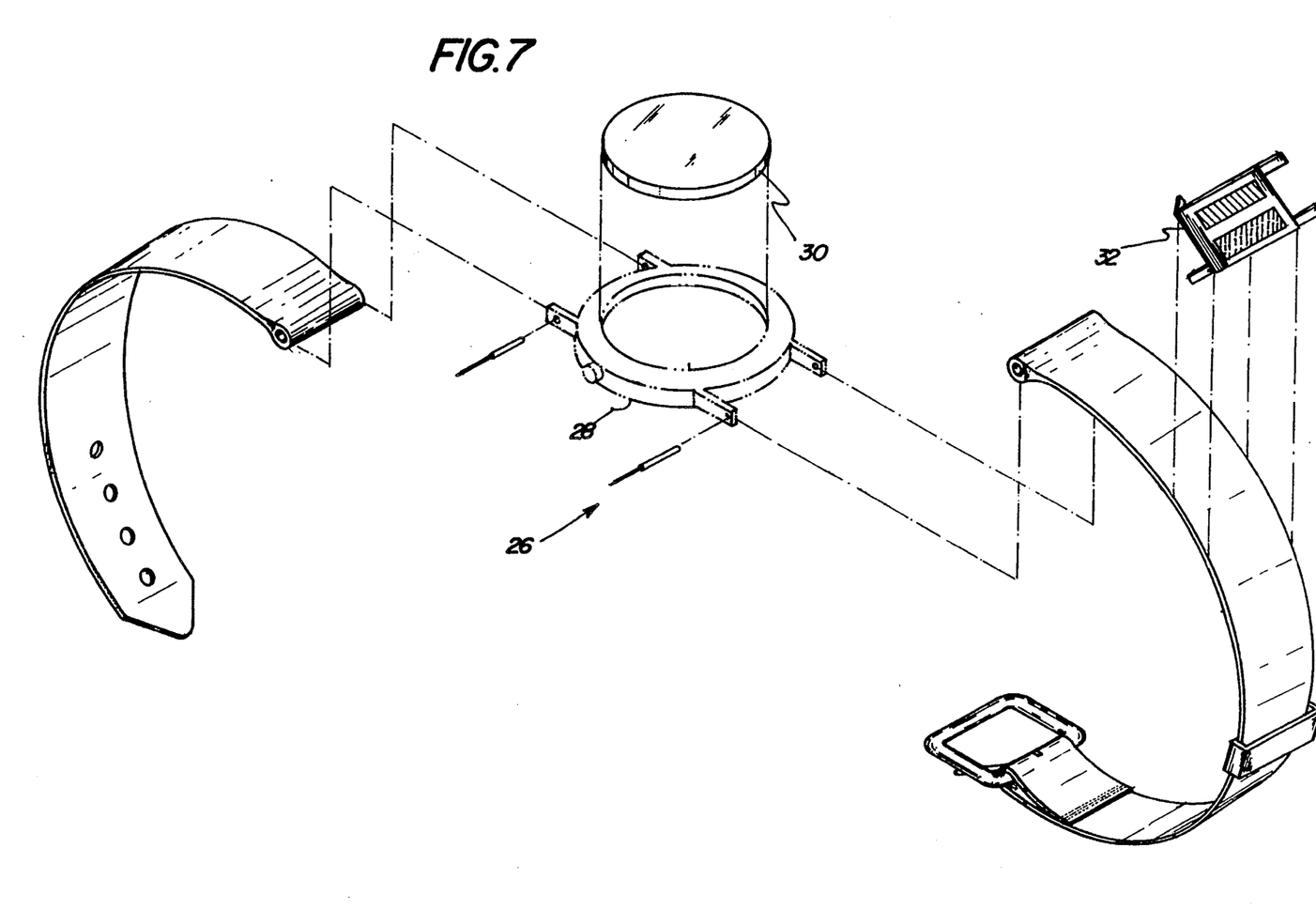
FIG. 7 is an exploded perspective view of a fourth embodiment of the harmful solar radiation detection device.

FIG. 7 of the drawings illustrate a fourth embodiment of the invention which is generally designated by the reference numeral 26. This fourth embodiment 26 is representative of the many different ways the present invention could be employed in everyday known structures. The embodiment 26 is shown encompassed in a conventional wristwatch 28 wherein the watch crystal 30 is impregnated with chemicals X and Y so as to be changeable in color as a result of detected solar radiation. Additionally, a clip-on watch band color chart 32 can be provided so that a user could compare a range of colors with the color of the crystal 30, thereby to determine the level of dangerous solar radiation.

As can be appreciated, the present invention has been described in its fullest known terms and manner of operation, and the invention is intended to encompass both the method of utilizing various chemicals capable of being combined to detect various levels of solar radiation and alternatively, to indicate the type of structure which would be used in combination with such chemicals in the event that such chemicals are not presently known in the prior art.

As to the manner of usage and operation of the present invention, the same should be apparent from the above description. Accordingly, no further discussion relating to the manner of usage and operation will be provided.

With respect to the above description, it should be realized that the optimum dimensional relationships for the parts of the invention, to include variations in size, materials, shape, form, function and manner of operation, assembly and use, are deemed readily apparent and obvious to those skilled in the art, and therefore, all relationships equivalent to those illustrated in the drawings and described in the specification are intended to be encompassed only by the scope of appended claims.

While the present invention has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein. Hence, the proper scope of the present invention should be determined only by the broadest interpretation of the appended claims so as encompass all such modifications and equivalents.

What is claimed as being new and desired to be protected by Letters Patent of the United States is as follows:

1. A harmful solar radiation detection apparatus, comprising:
   a first fluorescent composition comprised of a blend of a first fluorescent material and a second fluorescent material, said first fluorescent material capable of absorbing radiation having a wavelength less than 300 nm and capable of fluorescing at a first fluorescent wavelength above 300 nm upon absorption of said radiation less than 300 nm, said second fluorescent material capable of absorbing radiation at said first fluorescent wavelength and capable of fluorescing at a second fluorescent wavelength which is a visible wavelength,
   a second fluorescent composition comprised of said second fluorescent material,
   a first retainer for retaining said first fluorescent composition,
   a second retainer for retaining said second fluorescent composition, and
   a housing assembly for supporting and housing said first retainer and said second retainer such that said first fluorescent composition and said second fluorescent composition are capable of being exposed to sunlight.

2. The apparatus described in claim 1, further including:
   a first filter placed between sunlight and said first fluorescent composition, said first filter filtering out wavelengths above 300 nm,
   a second filter placed between sunlight and said second fluorescent composition, said second filter filtering out wavelengths above 300 nm, and
   a viewing window, defined by said housing assembly, for permitting a viewer to view said first fluorescent composition and said second fluorescent composition upon exposure to sunlight.

3. The apparatus described in claim 1 wherein said viewing window includes a magnifying member.

4. The apparatus described in claim 1 wherein:
   said first fluorescent material is composed of triphenylene which absorbs radiation below 300 nm and fluoresces at a first fluorescent wavelength at 365 nm, and
   said second fluorescent material is composed of 3-amino-fluoranthene which absorbs radiation at said first fluorescent wavelength and fluoresces at a second fluorescent wavelength at 515 nm, which is yellow in color.

5. A method of detecting harmful solar radiation, comprising the steps of:
   obtaining a quantity of a first fluorescent composition comprised of a blend of a first fluorescent material and a second fluorescent material, wherein the first fluorescent material is capable of absorbing radiation having a wavelength less than 300 nm and is capable of fluorescing at a first fluorescent wavelength above 300 nm upon absorbing the radiation less than 300 nm, wherein the second fluorescent material is capable of absorbing radiation at the first fluorescent wavelength and is capable of fluorescing at a second fluorescent wavelength which is a visible wavelength,
   obtaining a quantity of a second fluorescent composition comprised of the second fluorescent material,
   exposing both the first fluorescent composition and the second fluorescent composition to sunlight,
   comparing respective colors of the sunlight-exposed first fluorescent composition and the sunlight-exposed second fluorescent composition, such that the sunlight-exposed second fluorescent composition serves as a control, and the sunlight-exposed first fluorescent composition serves as an indicator of exposure to harmful solar radiation.

6. The method described in claim 1, further including the steps of:
   filtering sunlight through a first filter for providing the first fluorescent composition with filtered sunlight, wherein the first filter filters out wavelengths above 300 nm, and
   filtering sunlight through a second filter for providing the second fluorescent composition with filtered sunlight, wherein the second filter out wavelengths above 300 nm.

7. A solar radiation detection device comprising:
   housing means;
   crystal lattice structure means mounted in said housing means;
   first solar radiation sensing means forming a part of said crystal lattice structure means; and
   second solar radiation sensing means forming a part of said crystal lattice structure means,
   wherein said first solar radiation sensing means assumes a first color in response to a specific detected wavelength of solar radiation,
   and further wherein said second solar radiation sensing means assumes a second color in response to a second specific detected wavelength of solar radiation.

8. The solar radiation detection device as described in claim 7, wherein said first and second solar radiation sensing means are concurrently viewable in an overlying manner so as to provide a third specific color when said first and second specific colors are present, thereby to indicate one of a safe and unsafe suntanning condition.

9. A solar radiation detection device comprising:
housing means;
first crystal lattice structure means mounted in said housing means, said first crystal lattice structure means including first solar radiation sensing means; and
second crystal lattice structure means mounted in said housing means, said second crystal lattice structure means including second solar radiation sensing means, said second crystal lattice structure means being slidable within said housing means so as to be positionable over said first crystal lattice structure means by a user, thereby to facilitate a concurrent viewing of said first and second crystal lattice structure means.

10. The solar radiation detection device as described in claim 9, and further wherein said first crystal lattice structure means assumes a first color in response to a specific detected wavelength of solar radiation and further wherein said second crystal lattice structure means assumes a second color in response to a second specific wavelength of solar radiation, each of said first and second crystal lattice structure means respectively assuming different colors in response to detected solar radiation whereby an indication of a safe suntanning level is provided.

* * * * *